United States Patent [19]
Benedict et al.

[11] Patent Number: 5,108,923
[45] Date of Patent: Apr. 28, 1992

[54] BIOADHESIVES FOR CELL AND TISSUE ADHESION

[75] Inventors: Christine V. Benedict, Farmington; Paul T. Picciano, Canton, both of Conn.

[73] Assignee: Collaborative Research, Inc., Bedford, Mass.

[21] Appl. No.: 34,801

[22] Filed: Apr. 3, 1987

Related U.S. Application Data

[63] Continuation-in-part of Ser. No. 856,687, Apr. 25, 1986, abandoned.

[51] Int. Cl.$^5$ .................. C12N 5/00; C12N 11/00
[52] U.S. Cl. .................. 435/240.243; 435/240.1; 435/240.2; 435/240.21; 435/240.23; 435/174; 435/177; 435/180
[58] Field of Search .................. 435/4, 240.243, 240.1, 435/176, 174, 177, 178, 179, 180, 240.2, 240.23, 240.21; 424/77; 530/353, 857; 514/12, 21

[56] References Cited

U.S. PATENT DOCUMENTS 3,910,819 10/1975 Rembaum et al. ............ 435/240.243
4,119,589 10/1978 Horn et al. .................. 260/6

(List continued on next page.)

OTHER PUBLICATIONS

Picciano et al, "Mussel Adhesive Protein: A New Cell Attachment Factor", In Vitro: Cellular and Developmental Biology, vol. 22(3), p. 24A, Ab #55, Mar. 1986.

(List continued on next page.)

Primary Examiner—Elizabeth C. Weimar
Assistant Examiner—Gail Poulos
Attorney, Agent, or Firm—Wolf, Greenfield & Sacks

[57] ABSTRACT

A cell culturing system, methods for the preparation thereof, and methods for affixing other biologically active moieties to a substrate are provided. Said cell culturing system comprises: a substrate; a coating thereon of a sterile formulation comprising polyphenolic protein containing from about 35 to 100% by weight pure bioadhesive polyphenolic protein having the repeating decapeptide unit:

wherein N is a whole number ranging from about 10 to about 100, wherein each X is independently selected from the group consisting of hydroxyl and hydrogen, and wherein each R is independently selected from the group consisting of hydrogen and methyl; viable cells affixed to said coated substrate; and a nutritive medium contacting said cells, whereby said cells perform normal metabolic cell functions.

24 Claims, 3 Drawing Sheets

U.S PATENT DOCUMENTS

| | | | |
|---|---|---|---|
| 4,266,032 | 5/1981 | Miller et al. | |
| 4,352,887 | 10/1982 | Reid et al. | 435/240.1 |
| 4,496,397 | 1/1985 | Waite | 530/328 |
| 4,501,815 | 2/1985 | Reid et al. | 435/284 |
| 4,553,974 | 11/1985 | Dewanjee | 8/94.11 |
| 4,559,304 | 12/1985 | Kasai et al. | 435/240.243 |
| 4,578,079 | 3/1986 | Rouslahti et al. | 623/11 |
| 4,585,585 | 4/1986 | Waite | 530/353 |

OTHER PUBLICATIONS

Biopolymers, Inc., "Cell-Tak", Dec. 1986.
Biological Abstracts, vol. 77(3), #19656, Mills et al, 1983.
Chemical Abstracts, vol. 100, #56753y, Illum et al, 1984.
Gospodarowicz et al., "The Role of the Extracellular Matrix and Growth Factors in the Control of Proliferation of Anchorage-Dependent Cells", Prog. Cancer Res. Ther., vol. 23, 73-104, 1982.
Alitalo et al, "Extracellular Matrix Proteins of Human Epideraml Keratinocytes and Feeder 3T3 Cells", J. Cell. Biol., vol. 94, 497-505, 1982.
Foxall et al, "Adult Human Endothelial Cell Coverage of Small Caliber Dacron and Polytetrafluorolkylene Vascular Prosthesis In-Vitro", J. Surg. Res. vol. 41(2), 158-172, 1986.
Leivo et al, "Basal Lamina Glycoproteins Laminin and Type IV Collagen are Assembled into a Fine-Fibered Matrix in Cultures of a Teratocarcinoma-Derived Endodermal Cell Line", Exp. Cell Res., vol. 137(1), 15-23, 1982.
Hawrot et al., "Long-Term Culture of Dissociated Sympathetic Neutrons", *Methods in Enzymology*, vol. LVIII, pp. 574-584, 1979, Jakoby et al., ed. Academic Press.
Imagawa et al, "Isolation and Serum-Free Cultivation of Mammary Epithelial Cells within a Collagen Gel Matrix", *Methods for Serum-Free Culture of Cells of the Endocrine System*, Barnes et al., ed., pp. 127-441, 1984, Alan R. Liss, Inc., New York, N.Y.
Waite et al, "Polyphenolic Substance of Mytilus Edulis: Novel Adhesive Containing L-Dopa and Hydroxyproline", Science, vol. 212, pp. 1038-1040, 1981.
Collaborative Research, Inc. (Nov. 1983).
Bethesda Research Laboratories (1981/1982).
Sigma Chemical Company (Feb. 1985).
Biomatrix Product, pp. 10-13.
CalBioChem, "Extracellular Matrix Protein Research Aided by CalBioCHem Antibodies".
Sigma, "Tissue Culture Media and Reagents".
Telios, "Telios Pharmaceuticals Research Products".
McKeehan and Ham, "Stimulation of Clonal Growth of Normal Fibroblasts with Substrata Coated with Basic Polymers," J. Cell Biol. 71:727-734 (1976).
Waite, "Quinone-Tanned Schleroproteins" in 1 *The Mollusca, 467-504 (1981).*
*Science*, vol. 212, 1038-1040 (May 29, 1981).
"Nature's Underwater Adhesive Specialist", *Int. J. Adhesion and Adhesives*, vol. 7, NO. 1, 9-14 (Jan. 1987).
"Novel Materials from Protein-Polymer Grafts", *Nature*, vol. 325, 328-329 (Jan. 22, 1987).
"Mussel Glue From *Mytilus californianus* Conrad: A Comparative Study", *Journal of Comparative Physiology B*, vol. 156, 491-496 (1986).
"Assay of Dihydroxyphenlalanine (dopa) in Invertebrate Structural Proteins", *Methods in Enzymology*, vol. 107, 397-413 (1984).
"Catechol Oxidase in the Byssus of the Common Mussel", *Mytilus edulis* L., *J. Mar. Biol. Ass. U.K.*, vol. 65, 359-371 (1985).
"Evidence for a Repeating 3,4-Dihydroxyphenylalanine- and Hydroxyproline-Containing Decapeptide in the Adhesive Protein of the Mussel, *Mytilus edulis* L.", *Journal of Biological Chemistry*, vol. 258, No. 5, 2911-2915 (Mar. 10, 1983).
"Peptide Repeats in a Mussel Glue Protein: Theme and Variations", *Biochemistry*, vol. 24, 5010 (1985).
Ito et al, "Oxidation of Tyrosine Residues in Proteins by Tyrosinase", *Biochem. J.*, vol. 222, 407-411 (1984).
Ruoslahti et al., "Synthetic Peptides Causing Cellular Adhesion to Surfaces," Biotechniques, 38-41 (Jan./Feb. 1984).
Cook, M., "Composition of Mussel and Barnacle Deposits at the Attachment Interface," *Adhesion in Biologicals Systems*, 139-150 (Academic Press) (1970).
Gross and Hoffman, "Medical and Biological Adhesives," *Handbook of Adhesives*, 818-835 (2d. ed., van Nostrand Reinhold Co.) (1977).
Pierschbacher & Rouslahti, "Cell-Attachment Activity of Fibronectin can be Duplicated by Small Synthetic Fragments of the Molecule", *Nature*, vol. 309, No. 5963, pp. 30-33, (May 1984).

BIOADHESIVES FOR CELL AND TISSUE ADHESION

CROSS-REFERENCE

This application is a continuation-in-part of co-pending patent application Ser. No. 856,687, filed on Apr. 25, 1986 now abandoned.

FIELD OF THE INVENTION

This invention relates to the use of bioadhesive polyphenolic proteins to promote adhesion of cells, tissues and other biologically active moieties to a variety of substrates. In this context, "Bioadhesive" refers to an adhesive that is compatible with the metabolism, growth or function of living tissues, cells, and other biologically active moieties in vitro or in vivo. Bioadhesive polyphenolic proteins are based on the sequence of repeating decapeptides having the formula:

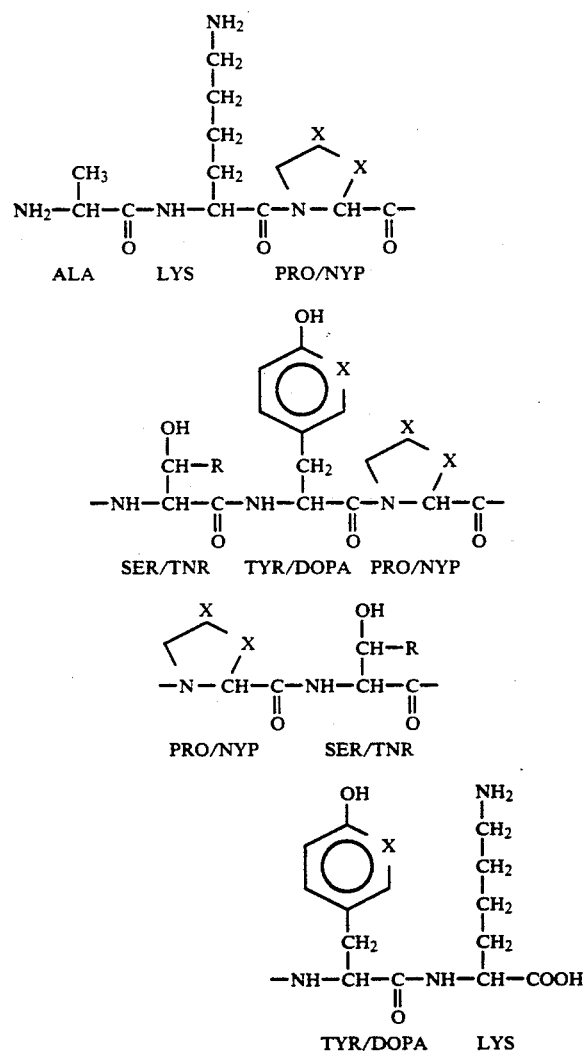

as described in U.S. Pat. No. 4,585,585 entitled "Decapeptides Produced From Bioadhesive Polyphenolic Proteins". Bioadhesives produced from the repeating decapeptides are ideal because they now have been found to enable cells and other biologically active moieties, such as proteins, DNA, hormones and antibiotics to attach to virtually any substrate. Applications in vitro include research diagnostics, cell product harvest, and cell metabolism research. In vivo applications include the production of confluent cell monolayers on the surface of prostheses, especially cardiovascular prostheses.

DESCRIPTION OF THE PRIOR ART

The harvest of cells from tissue for maintenance and propagation in vitro by tissue culture is a major tool in medical and biochemical research. Tissue culture is the technique or process of propagating and/or supporting the metabolism of tissues or cells derived from organisms (plant or animal) in a formulated nutritive environment. Once isolated by gentle tissue dissociation, cells are incubated in nutritive media capable of supporting life functions. With few exceptions, cells require attachment to a substratum in order to perform normal metabolic functions, grow and divide. In tissue, the substratum which provides the matrix for cell growth consists of collagen, laminin, and fibronectin. In vitro, this substratum is most often plastic, although glass and microporous cellulosic filters are sometimes used as substitutes. Examples of cell uses produced via tissue culture include: (1) the study of the metabolism of the cell, the metabolism of parasites (i.e., viruses, bacteria, etc.) within the cell, the interactive metabolism of different cell types (i.e., epithelial cells, fibroblasts, immunocompetent cells, thymocytes, platelets, etc.), the effect of exogenous factors on cellular metabolism, the genetic composition of cells (in vitro diagnostics); (2) the production of specific compounds, i.e., genes, proteins or other cellular components; and (3) the re-implantation of cells as for skin, corneal grafts, brain, vascular grafts, and in vitro fertilization.

In recent years, collagen, laminin, and fibronectin have been extracted and purified from animal tissues and marketed to cell and tissue culture researchers as cellular adhesion promoters. Synthetic poly-D-lysine and poly-L-lysine have also been sold for such purposes. The primary reason for this is that, in vitro, substrates such as plastic or glass are biologically inert and often do not provide sufficient substrate adhesion for adequate cell or tissue attachment. Specific examples illustrative of poor attachment efficiency include primary cell isolates, cells seeded at low densities and cells seeded in continuous flow systems such as bio-reactors or hollow tube culture systems. In addition, certain substrates such as some microporous filters or Teflon ® materials used for vascular grafts do not permit any cell attachment due to low surface energy.

Although adhesion promoters have assisted with attachment problems to a significant degree, certain inadequacies are still noteworthy. First, their mode of action is based on the fact that, although physiological, these factors are not truly adhesive; they only provide a physical support and trapping for cells. Second, they are not easily utilized on a variety of substrates other than those conventionally used for cell culture (e.g., polystyrene, nitrocellulose) nor can each be used with equal effectiveness for all cell types. Third, once reconstituted, most of these factors have a shelf life of approximately 4 weeks at −20° C. Fourth, with the exception of poly-D- and poly-L-lysine, these factors must be extracted from biological sources; they cannot be synthesized within commercially acceptable costs. Fifth, a recognizable potential health hazard arises with certain cellular adhesion promoters, including, for example, the extraction of fibronectin from human blood.

For in vivo applications, confluent cell monolayers are desired on prostheses, especially cardiovascular prostheses. Endothelial cells normally line the lumen of such vessels and actively prevent thrombosis, which is a major problem in the management of patients with cardiovascular disease. These cells also produce basement membrane material, the matrix for further wound healing. Currently, these prostheses are made of Teflon ®, a substrate which does not promote cell attachment. No other known attachment factor mediates cell attachment to Teflon ®.

The use of bioadhesive polyphenolic proteins obviates these problems. It attaches well to a variety of substrates in the presence of water and does not fail in a continuously humid environment. Being a true adhesive, bioadhesive polyphenolic protein rapidly attaches to both substrates and a variety of cells, tissues and other biologically active moieties. It can be stored at 4° C. for at least 10 months and at room temperature for at least 1 month without degradation or loss of function. Further, it can be synthesized by solid phase peptide synthesis, or via a genetic engineering approach, thereby permitting greater standardization of large quantities.

The repeating decapeptide structure of bioadhesive polyphenolic proteins derived from the marine mussel is described in U.S. Pat. No. 4,585,585, "Decapeptides Produced from Bioadhesive Polyphenolic Proteins". Formulations of bioadhesive polyphenolic proteins and methods for production of bioadhesive polyphenolic proteins are the subject of co-pending patent applications. Methods for the preparation of bioadhesive polyphenolic proteins are known in the art (Waite & Tanzer, 1981, Science 212, 1038).

It is, thus, one object of the present invention to provide preparations useful as adhesive factors to promote or augment attachment efficiency, rate and/or strength of adhesion, growth and specialized function of cells to tissue culture or non-tissue culture materials and substrates including plastic, glass, metals, microporous filters (cellulosic, nylon, glass fiber, polyester, polycarbonate, polyethylene terephthalate and other synthetic and nonsynthetic materials including other synthetic polymeric materials and products resulting from modifications made to the aforementioned synthetic polymeric materials) and synthetic or alloplastic materials that may be used in tissue or prosthetic graft procedures (e.g., mechanical heart and polytetrafluoroethylene and related vascular grafting materials).

A second object of the present invention is to provide preparations useful as adhesive factors to promote or augment attachment efficiency, rate and/or strength of adhesion of other biologically active moieties such as proteins, DNA, hormones and antibiotics to a variety of substrates, some of which are mentioned above.

A third object of the present invention is to provide the preparation or layering of substrates with bioadhesive polyphenolic proteins and the assays employed to investigate the effectiveness of such layers on the above-mentioned parameters.

SUMMARY OF THE INVENTION

The foregoing and other objects, advantages, and features of this invention are accomplished by the present invention which provides a method of affixing viable cells, tissues and other biologically active moieties such as proteins, DNA, hormones and antibiotics, to a substrate comprising:

(1) coating a substrate with a sterile formulation comprising polyphenolic proteins containing from about 35 to 100% by weight pure bioadhesive polyphenolic protein having the repeating decapeptide unit:

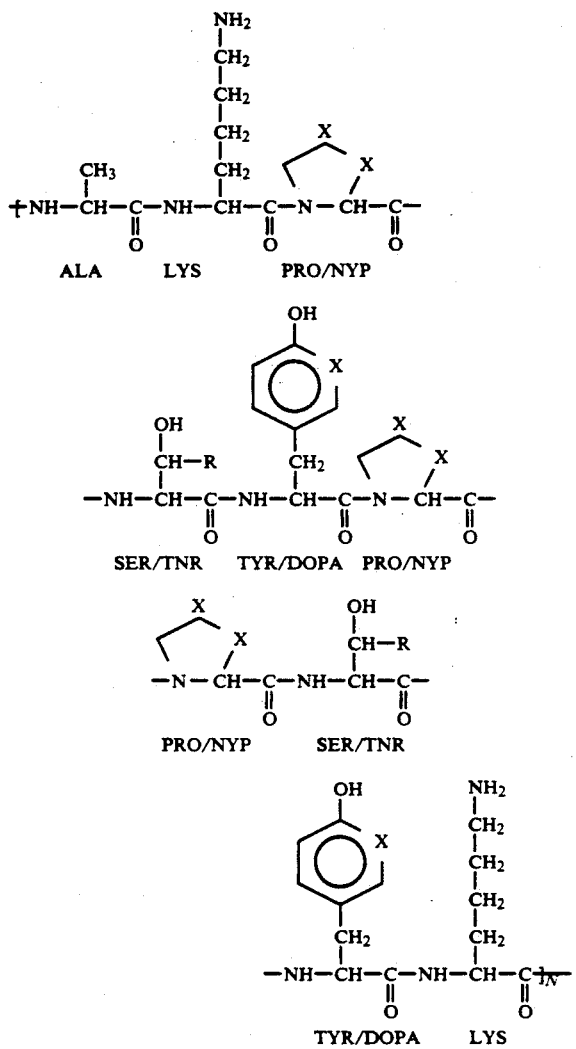

wherein N is a whole number ranging from about 10 to about 100, wherein each X is independently selected from the group consisting of hydroxyl and hydrogen, and wherein each R is independently selected from the group consisting of hydrogen and methyl;

(2) drying said coating on said substrate;
(3) fixing said coating on said substrate;
(4) rinsing said coated substrate to remove extraneous materials not firmly attached to said substrate; and
(5) applying viable cells, tissues or other biologically active moieties to said coated substrates, whereby said moieties become affixed to said coated substrate. Concentrations and formulations of the bioadhesive polyphenolic protein may be altered according to substrate type or the attachment requirements of the particular cell, tissue or biologically active moiety employed. When affixing viable cells, the presence of a nutritive environment is required in order for the cells to perform their normal metabolic cell functions.

The present invention will become more readily understood by reference to the drawings which describe in detail one representative embodiment of the present invention wherein.

Figure 4:
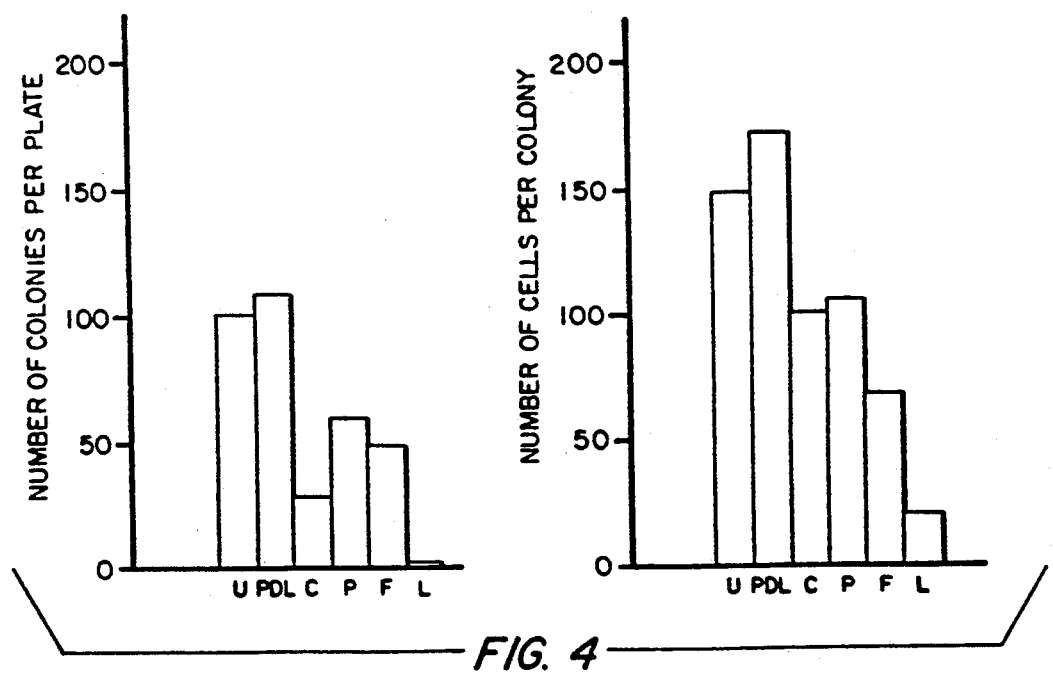
Figure 5:
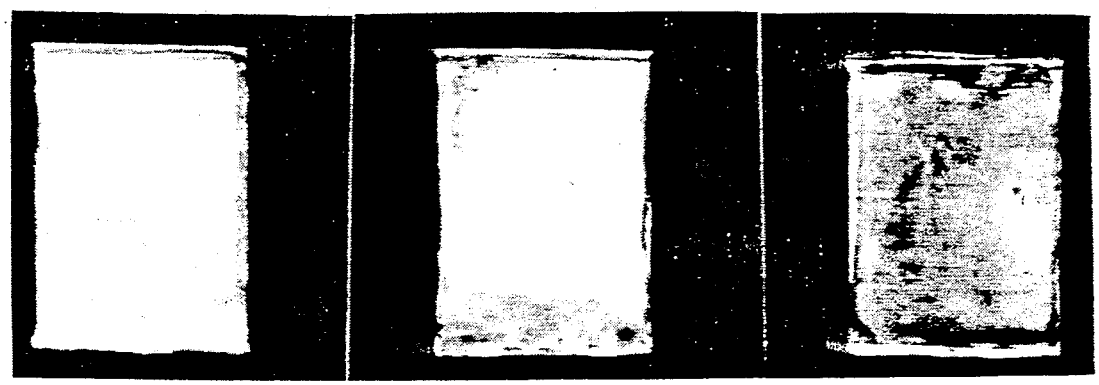

FIG. 4 is a graphical representation of the data generated in Example 4 showing, by bar graphs, both the number of colonies per plate and the average number of cells per colony for each of the factors evaluated; and FIG. 5 is a photograph of three samples of polytetrafluoroethylene (PTFE) after staining with crystal violet: Sample 1 (the sample on the left) is PTFE coated with Formulation 2; Sample 2 (the center sample) is PTFE seeded with cells, but not coated with Formulation 2; and Sample 3 (the sample on the right) is PTFE coated with Formulation 2 and seeded with cells.

DETAILED DESCRIPTION OF THE INVENTION

The growth and normal metabolism of eukaryotic cells requires attachment to a substrate with the cell layer essentially extended face-to-face on the substrate. Conventionally, cell culture utilizes plastic substrates and, to a lesser degree, glass and microporous filters for cell attachment and propagation. More recently, physiological substrates (collagen, laminin, fibronectin, poly-D- and poly-L-lysine) have been utilized for these purposes in lieu of plastic to avoid problems inherent in cell culture at low seeding densities, using freshly isolated cells or on substrates less suitable for attachment (e.g., Teflon ®). Bioadhesive polyphenolic proteins provide a suitable alternative because of their high binding affinity for both cells and a variety of substrates, biological and inert.

Bioadhesive polyphenolic protein formulations have been evaluated for their efficiency in binding cells in vitro for cell culture. The formulations tested have included (1) 95% pure bioadhesive polyphenolic protein prepared from natural sources ("Formulation 1") and (2) 45% pure bioadhesive polyphenolic protein prepared from natural sources ("Formulation 2").

After preparing bioadhesive polyphenolic proteins according to procedures described in U.S. Pat. No. 4,585,585, these formulations were thoroughly characterized biochemically using high performance liquid chromatography, assays for the quantitation of L-dopa, amino acid analysis and polyacrylamide gel electrophoresis. The composition of key amino acids in the bioadhesive polyphenolic protein formulations is given in Table 1.

TABLE 1

Amino Acid Composition of Bioadhesive Polyphenolic Proteins in Residues per 1,000 Residues

|  | (1) 95% Bioadhesive Polyphenolic Protein | (2) 45% Bioadhesive Polyphenolic Protein |
| --- | --- | --- |
| 3-hydroxyproline | 27 | 4.3 |
| 4-hydroxyproline | 88 | 33.4 |
| proline | 79 | 72.5 |
| glycine | 51 | 138.3 |
| 1/2 cystine | 9 | 7.7 |
| L-3,4-dihydroxyphenylalanine | 96.5 | 42.3 |
| tyrosine | 54 | 39.3 |
| lysine | 175 | 103.9 |

In Formulation 2, collagen comprises the majority of the remaining 55%. The basic unit of the bioadhesive polyphenolic protein is a decapeptide (chain of 10 amino acids) which is repeated through covalent bonds to similar decapeptides as many as 75–85 times. These formulations, based on bioadhesive polyphenolic protein, are stable, based on adhesive functionality, at 4° C. in 5% (v/v) acetic acid, pH 2.8 for greater than 10 months. Extracted preparations containing 40 to 50% collagen are stable at room temperature in 5% (v/v) acetic acid, pH 2.8 or following drying onto plastic substrates for at least 2 months.

The ability of bioadhesive polyphenolic protein to strongly attach to a variety of substrates permits the attachment, maintenance and growth of cells to surfaces that heretofore posed problems either because of their composition, their application, or the type of cell requiring attachment. Substrates that could be used include plastic, glass, and microporous filters (e.g., cellulosic, nylon, glass fiber, polyester, polycarbonate) for conventional cell culture research and/or cell product harvesting from bio-reactors used in batch cell culture or in genetic engineering; hollow fiber tubes for cell product harvesting; and prosthetic vascular graft materials such as polytetrafluoroethylene (Teflon ®) and related materials. Most of these surfaces carry a net negative charge and, therefore, tend to bind tightly net positively charged materials such as bioadhesive polyphenolic proteins. Cells carry a net negative charge and, as a result, are slightly repelled from untreated surfaces while being attracted to the intermediary bioadhesive polyphenolic protein which has a net positive charge. Bioadhesive polyphenolic protein would increase attachment efficiency, attachment rate and strength of attachment. This latter parameter is critical in applications involving cell product harvesting procedures or re-implantation of cells on vascular grafts which involve the passage of fluids over cell monolayers. Moreover, cells that attach poorly following isolation from tissue or due to cell type, and cells that do not normally attach, such as blood cells and suspension tissue culture cells (histiocytic lymphomas, platelets, white and red blood cells, etc.) could also be attached to substrates through this intermediate.

Furthermore, the ability of bioadhesive polyphenolic protein to strongly attach to a variety of substrates permits the attachment of many other biologically active moieties, such as DNA, proteins, hormones and antibiotics.

The coating of substrates with bioadhesive polyphenolic protein formulations and attachment to substrates is generally performed as follows. Depending on the final concentration per square cm desired, about 1 to 2 μl of sterile bioadhesive polyphenolic protein ranging from 10 to 60 μg per μl are evenly applied per cm² of substrate. The resultant film is dried rapidly by placing the substrate within a laminar flow hood. Once dried, the film is treated with 35-100% ethanol or isopropanol for rinsing and fixation and then with sterile tissue culture medium for removal of residual alcohol and nonadsorbed extraneous moieties. The substrate may be used immediately or dried for storage. Cells or other biologically active moieties to be attached to the film are adjusted to desired concentrations and added to the substrate in serum-free or serum-containing medium. In the case of attachment of cells, at various timed intervals, the cells are evaluated for attachment, growth, or function, or treated according to prescribed objectives of experiments requiring the attached cells in tissues culture.

Conversely, when desirable, the bioadhesive polyphenolic protein can be affixed to the biologically active moieties and then, the resultant biologically active moieties can be affixed to the substrate. The foregoing method, in greater detail, comprises the steps of:

(1) dispersing said biologically active moieties in a serum-free solution;

(2) admixing a sterile formulation comprising polyphenolic protein containing from about 35 to 100% by weight bioadhesive polyphenolic protein having the repeating decapeptide unit:

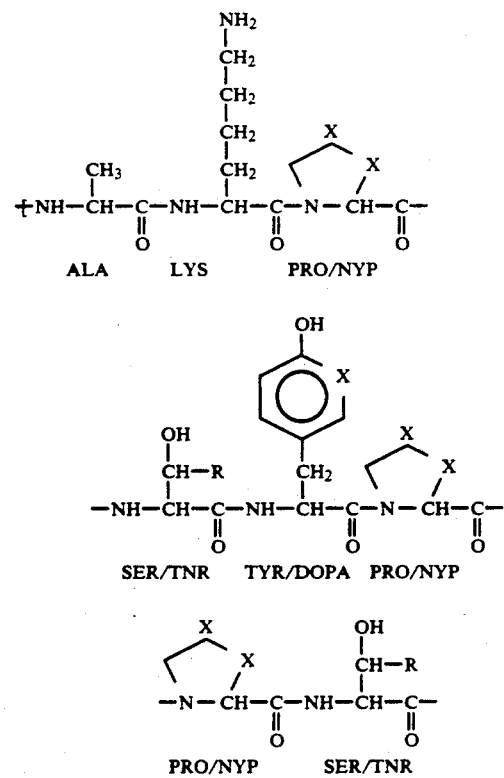

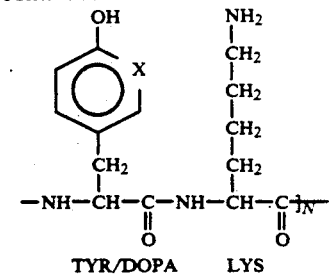

wherein N is a whole number ranging from about 10 to about 100, wherein each X is independently selected from the group consisting of hydroxyl and hydrogen, and wherein each R is independently selected from the group consisting of hydrogen and methyl; with said dispersion of biologically active moieties, thereby attaching said bioadhesive polyphenolic protein to said biologically active moieties;

(3) recovering the resulting biologically active moieties; and (4) affixing said recovered biologically active moieties to said substrate.

EXAMPLE 1

Assessment of Cell Binding Efficiency

Formulations containing either 95% bioadhesive polyphenolic protein (Formulation 1) or 45% bioadhesive polyphenolic protein (Formulation 2) were evenly layered on 35 mm tissues (9 cm²) culture plastic petri dishes at 50 μg per dish in 5% (v/v) acetic acid, dried rapidly, "fixed", and sterilized by rinsing with 100% ethanol. Dishes were then rinsed with sterile triple distilled water.

Cells were prepared for the attachment assay as follows. Bovine corneal endothelial cells were treated with trypsin, a protease which digests cell attachment proteins, following growth in subculture in 5% CO₂ in air at 37° C. in a humidified incubator. Cell monolayers were rinsed with serum-free medium to remove excess serum and medium that might interfere with trypsinization and incubated with 0.05% trypsin-0.02% ethylene diamine tetraacetic acid (EDTA) for 10 minutes. Cells detached by the action of trypsin were transferred by pipette and gently centrifuged at 250×g. Resultant pellets were re-suspended in serum-free minimal essential medium (Earle's salts) to remove any remaining serum proteins and trypsin from cell surfaces and again centrifuged.

Viable cell counts were obtained using a dye exclusion test, where representative aliquots of cells were then re-suspended to a final concentration of 2×10⁵ cells per ml in minimal essential medium containing 15% fetal bovine serum. Cells were seeded in untreated plastic tissue culture petri dishes (control) and in tissue culture dishes layered with bioadhesive polyphenolic protein. At 1, 2.5, 5, 12.5, and about 20 min., triplicate experimental and control plates were chosen at random for quantitation of unattached cells. Unattached cells were removed from plates by rinsing and counted on a hemacytometer; replicate aliquots of cells that had been used, but that had not been added to dishes, were also counted in triplicate. Data were calculated as percent of cells attached by subtracting the number of unattached cells harvested from each dish from the total number of cells plated.

Figure 1:
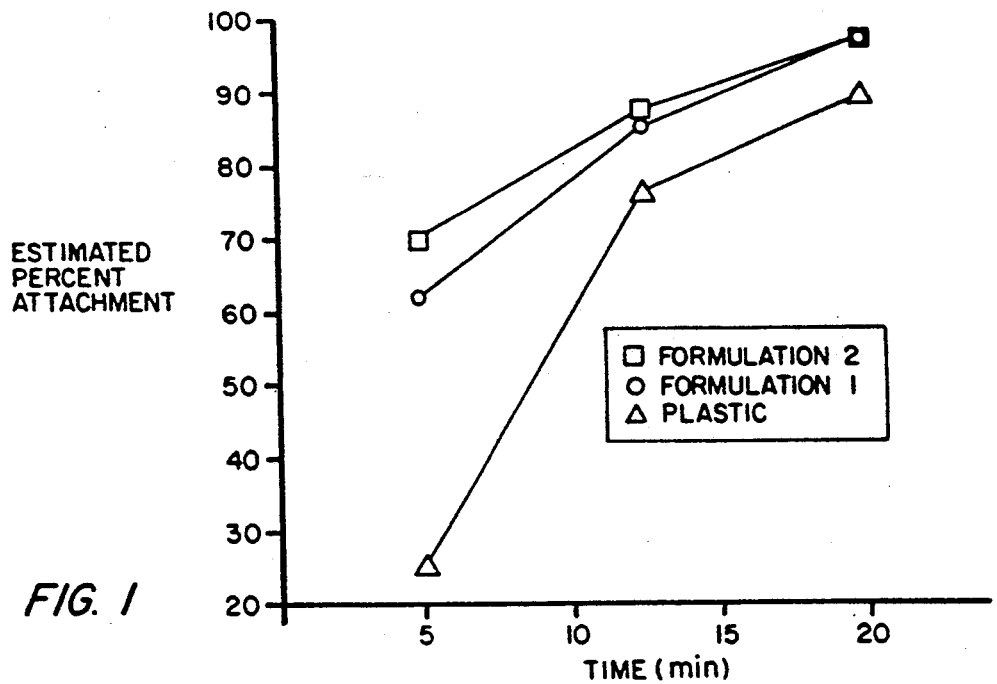
FIG. 1 is a graphical representation of the data generated in Example 1 showing the estimated percent of cell attachment versus time in minutes.

Comparison of data showing percent of attachment of cells to bioadhesive formulations are found below in Table 2 and shown graphically in FIG. 1.

TABLE 2

Comparison of Attachment on Plastic and Formulations 1 and 2

| Time(minutes) | Variable | Percent Estimated Attachment |
|---|---|---|
| 5.0 | Plastic | 25 |
|  | Formulation 1 | 62 |
|  | Formulation 2 | 70 |
| 12.5 | Plastic | 76 |
|  | Formulation 1 | 85 |
|  | Formulation 2 | 87 |
| 20.0 | Plastic | 89 |
|  | Formulation 1 | 97 |
|  | Formulation 2 | 97 |

It can be seen that, within only 5 minutes, the attachment of cells in Formulation 2 (i.e., higher collagen content) is more than 2-fold greater than the attachment of cells to plastic. Further, at all time points, the binding capacity of cells to bioadhesive polyphenolic protein exceeds that of cells to plastic. Although results are similar for Formulation 1, other data suggest that Formulation 2 is preferable as a cell attachment factor and tissue culture tool.

Formulation 2 is very stable upon long-term storage. When tested by amino acid analysis, the L-dopa to protein ratios remained stable for Formulation 2 after 4 months at 4° and −20° C.; whereas, a decline of up to 25% is found under similar conditions with Formulation 1 (Table 3).

TABLE 3

Percent of Bioadhesive Polyphenolic Protein Remaining With Time at 4° C. and −20° C. Storage (Determined by Amino Acid Analysis)

|  | Formulation 1 | | Formulation 2 | |
|---|---|---|---|---|
|  | 3 months | 4 months | 3 months | 4 months |
| 4° | 97% | 76% | 100% | 98% |
| −20° | 97% | 82% | 104% | 100% |

Since stability of moieties at the biochemical level is highly desirable in tissue culture systems, it was concluded that Formulation 2 is preferred for purposes of enhancing cell attachment efficiency.

EXAMPLE 2

Effect of Serum on Cell Binding Strength and Efficiency

Depending on the objectives of an experiment or assay, more or less serum may be required during and after cell attachment. The effect of serum on cell binding and strength was tested using cells in medium containing 15% bovine serum (FBS) or 0.5% bovine serum albumin (BSA). Bovine serum is the major protein constituent found in FBS. Strength of attachment was indirectly evaluated by the ability or inability to remove attached cells by trypsin from substrates to which they were attached. The concentration of bovine serum albumin employed was equivalent to that found in 0.5% to 1% FBS. The coating of tissue culture petri dishes with Formulation 2 of bioadhesive polyphenolic protein was accomplished as in Example 1. Cells were seeded on plastic and adhesive-coated petri dishes in triplicate and the unattached cells were removed by rinsing at 2.5, 5, and 15 minutes. Unattached cells were trypsinized using 0.8 ml of 0.05% trypsin-0.02% EDTA for 10 minutes and transferred to tubes containing 0.2% FBS to inhibit further action of the trypsin on the cells. Recovered attached and unattached cells were counted using a hemacytometer and the data representing attached cells were calculated as a percentage of the total cells recovered from each of the dishes. This data is summarized in Table 4.

TABLE 4

Effect of Serum on Recovery of Cells From Plastic and Bioadhesive Polyphenolic Protein

| Time (Min) | Variable | % Attachment | % Cells Recovered | % Estimated Attachment |
|---|---|---|---|---|
| 2.5 | FBS-Plastic | 2 | 100 | 2 |
|  | FBS-Bioadhesive | 2 | 85 | 2 |
|  | BSA-Plastic | 6 | 79 | 26 |
|  | BSA-Bioadhesive | 31 | 105 | 28 |
| 5.0 | FBS-Plastic | 5 | 82 | 22 |
|  | FBS-Bioadhesive | 49 | 99 | 50 |
|  | BSA-Plastic | 31 | 51 | 65 |
|  | BSA-Bioadhesive | 28 | 60 | 56 |
| 15.0 | FBS-Plastic | 65 | 83 | 71 |
|  | FBS-Bioadhesive | 74 | 74 | 81 |
|  | BSA-Plastic | 40 | 33 | 77 |
|  | BSA-Bioadhesive | 62 | 39 | 85 |

Figure 2:
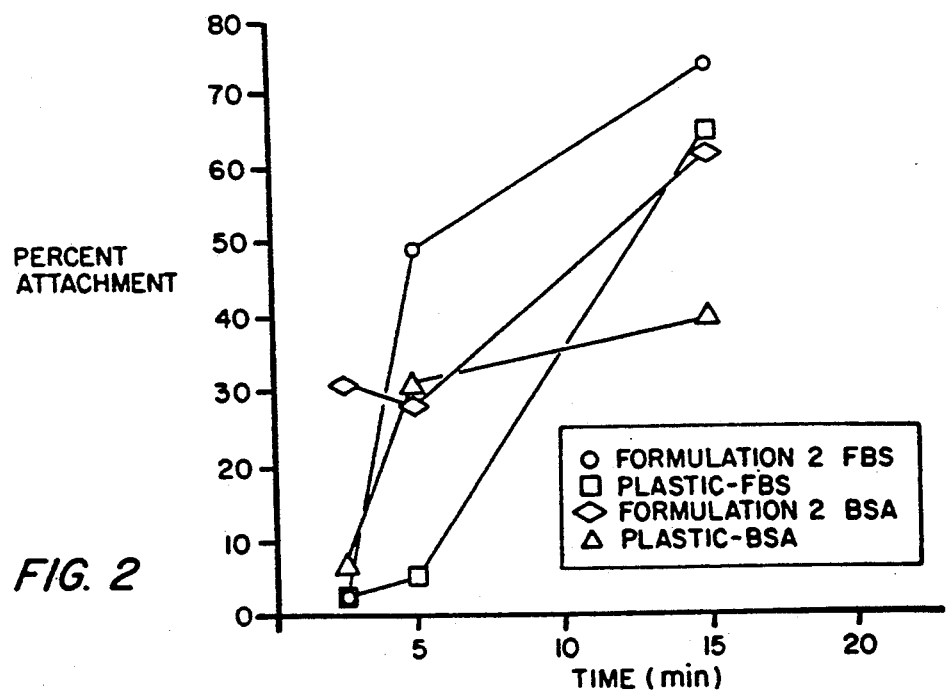
FIG. 2 is a graphical representation of the data generated in Example 2 showing the percent cell attachment versus time in minutes.

As can be seen from the data in Table 4, cells attach more strongly at early time periods on bioadhesive polyphenolic protein than to plastic. It can also be seen that if FBS in the medium is replaced with bovine serum albumin, a decreased recovery of cells by trypsinization results. This is especially seen at times when cells are establishing firm anchorage (5 minutes) and beginning to flatten (15 minutes). At 15 minutes, as low as 33% and 39% recovery was achieved with BSA on plastic and adhesive-coated petri dishes as compared with 83% and 74% recovery with FBS on plastic and adhesive cultures, respectively. Visual microscopic observations of plates confirmed these findings. Other findings in this study demonstrate that the direct evaluation of cell attachment described in this example strongly correlates with indirect measurement by counting unattached cells only (see Example 1 for counting details). FIG. 2 graphically illustrates these findings.

EXAMPLE 3

Attachment of Nonattaching Cells to Bioadhesive Polyphenolic Protein

The majority of cell types harvested from tissue following dissociation, when placed into cell culture, are capable of attaching to plastic substrates with varying degrees of efficiency. Certain cell types, however, do not attach to plastic substrates. The ability to attach such cells could be advantageous in that it would provide a means for diagnostic and research assays requiring the immobilization of these cells, and the ability to secure cells to bio-reactor filters for harvesting cell products. Furthermore, it would provide an unequivocal demonstration of the potential for bioadhesive polyphenolic protein to act as a tissue culture attachment factor.

The cell line U937 is a human histiocytic lymphoma that was established from malignant cells isolated from a pleural effusion. These cells grow in suspension continuously in RPMI 1640 tissue culture medium, supplemented with 10% fetal bovine serum. U937 cells attach poorly to plastic in the presence of serum.

Figure 3:
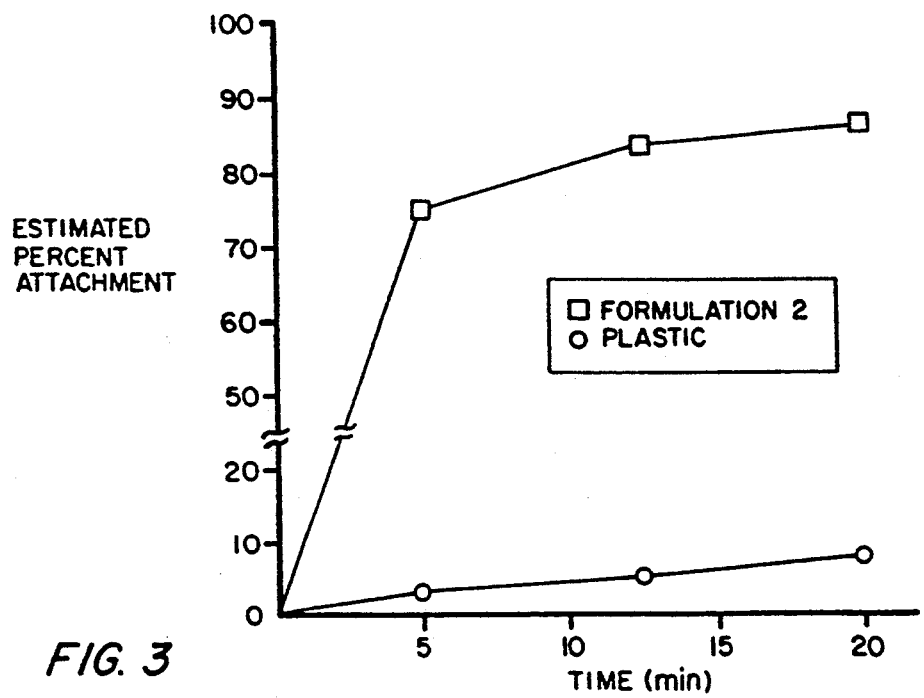
FIG. 3 is a graphical representation of the data generated in Example 3 showing the estimated percent of cell attachment versus time in minutes.

Tissue culture petri dishes (35 mm dishes) were coated with bioadhesive polyphenolic protein according to procedures outlined in Example 1. U937 cells were transferred to centrifuge tubes and prepared in the manner described in Example 1. Cells were seeded on plastic tissue culture dishes and on dishes coated with 100 μg of bioadhesive polyphenolic protein (Formulation 2), and evaluated in triplicate for attachment efficiency, (see Example 1) at 5, 12.5, and 20 minutes. The results in Table 5 (which are shown graphically in FIG. 3) clearly demonstrate the effect of bioadhesive polyphenolic protein on attachment of U937 cells. As expected, the cells attached poorly to the plastic dishes which served as controls; but within 5 minutes, 75% of the cells seeded had attached to coated dishes, and within 20 minutes, 87% of the cells attached to the coated dishes.

TABLE 5

| Time (minutes) | Percent Attachment of U937 Cells | |
| --- | --- | --- |
| | Uncoated Plastic | Plastic coated with Formulation 2 |
| 5 | 3% | 75% |
| 12.5 | 5% | 84% |
| 20 | 8% | 87% |

EXAMPLE 4

Comparison of Cell Growth on Bioadhesive Polyphenolic Protein and Commercially Available Cell Attachment Factors The attachment of cells to a substrate is only the first requirement for establishing cells in cultures in vitro. The second, and perhaps more important, requirement is that the cells grow. With the dissociation of tissue, however, the number of cells harvested is frequently very low. Low cell seeding numbers can adversely affect the establishment of cultures because fewer cells decrease the chance of survival for attachment. This is based on simple mathematical probabilities and on the need for metabolites produced by the cells themselves (density-dependent metabolites) which are required for cell attachment and growth. When cell numbers are low, probabilities are lower that adequate numbers of cells will attach, which itself is necessary for flattening of the cells onto the substrate from a spherical shape. Once flattened, metabolism may then ensue to further condition the medium for cell growth and division.

To enhance the attachment and propagation of cells that either do not readily attach and/or that are seeded at low densities, various peptide and protein attachment factors have been made available commercially. These include collagen, laminin, poly-D-lysine, and fibronectin. All of these factors work on biologically inert substrates to varying degrees, depending on the cell type seeded. To compare the effectiveness of bioadhesive polyphenolic protein to these factors in permitting growth at low seeding densities, bovine corneal endothelial cells were seeded at a density of 250 cells per tissue culture petri dish (35 mm diameter, 9.65 cm$^2$) on either plastic, bioadhesive polyphenolic protein, collagen, laminin, poly-D-lysine, or fibronectin. The cells were allowed to grow for 5 days, at which time colony sizes (number of cells per colony) and numbers of colonies per plate were evaluated for each of the variables by staining the cells with crystal violet. Data obtained were used to determine the effect of each of these factors on attachment (number of colonies) and growth (size of colonies).

Cells and dishes coated with bioadhesive polyphenolic protein were prepared as described in Example 1. The coating of dishes with other attachment factors was effected according to procedures suggested by their manufacturers.

Collagen—Collagen-coated plates were prepared by diluting 1 part cold (4° C.) collagen dispersion into 6 parts of cold 50% methanol. This mixture was mixed vigorously for several minutes and pipetted onto a petri dish so that only the bottom of the dish was covered. Within 20 seconds, the collagen was removed by aspiration and the dish was tilted upside down at 30° against a lid to dry. Following 1 hour of drying undisturbed in a laminar flow hood, the dishes were ready for use.

Laminin—Laminin is supplied in 1 mg quantities in 1 ml of 50 mM tris(hydroxymethyl)aminomethane in physiological saline. Following a slow thaw of laminin solution at 0° to 4° C. from −20° C., 10 to 15 μg of laminin solution was pipetted into petri dishes in 0.5 ml of 0.01M sodium phosphate buffer, pH 7.4. The dishes were dried at 37° C. Immediately upon drying, the dishes are prepared for use.

Fibronectin—Fibronectin is supplied in 1 mg quantities as a lyophilized powder. Prior to use, fibronectin is allowed to equilibrate to room temperature after storage at 4° C. The powder is reconstituted with 1 ml sterile distilled water and allowed to stand for 30 minutes for solubilization. Ten to 20 μg of fibronectin solution is added to each dish in 0.5 ml and allowed to air dry. At this time, the dish is ready for cell seeding.

Poly-D-lysine—Poly-D-lysine is supplied in quantities of 5 mg of lyophilized powder. prior to use, this powder is allowed to equilibrate to room temperature following storage at 4° C. Dishes are coated with 50 mg in 1 ml of sterile distilled water and allowed to stand at room temperature for 5 minutes. At that time, the solution is aspirated and the dishes are rinsed two times with 1.5 ml sterile distilled water. Following each rinse, liquid is aspirated completely. The dishes are dried and used immediately.

The plating efficiency of the cells seeded on each of the factors is evaluated following crystal violet staining of the cells. This is achieved by first rinsing the dishes containing the colonies with serum-free medium to remove excess proteins and fixing the cells with 10% neutral buffered formalin for 10 minutes. The formalin is then removed from the plates by aspiration and 0.1% crystal violet in tapwater is then added to the plates for a period of 7 minutes. Immediately following staining, crystal violet is poured off and the cells are rinsed in a beaker of running tapwater to remove excess stain. Following complete drying of the plates, colonies on duplicates representing each of the variables are counted; and cells in ten randomly selected colonies per plate are counted. The data obtained from this example appear in Table 6 and are graphically illustrated in FIG. 4 as bar graphs. As can be seen, the number of colonies in FIG. 4 on plates coated with bioadhesive polyphenolic protein (U) is matched only by poly-D-lysine (PDL). All other factors, including collagen (C), plastic (P), fibronectin (F), and laminin (L), yield poor results by comparison. Similarly, the average number of cells per colony found on plates coated with bioadhesive polyphenolic protein is matched by poly-D-lysine. Collagen, plastic, fibronectin, and laminin demonstrate poor efficiency in growth. Although no significant differences were found between bioadhesive polyphenolic protein and poly-D-lysine (possibly due to the high level of lysine found in each of these molecules), the use of bioadhesive polyphenolic protein as an attachment factor is nonetheless more advantageous as a substrate based on its ability to (1) displace water, (2) to attach to materials including metal and Teflon ® (for example, prosthetic devices), (3) to be used in vivo and in vitro, and (4) to form high strength bonds based on L-dopa, hydroxylated and lysine amino acid residues.

TABLE 6

Colony Number and Size Following Cell Growth on Various Tissue Culture Substrates

| | Colonies Per Variable-Day 5 | Average No. Cells Per Colony |
|---|---|---|
| Formulation 2 | 100 | 147 |
| Poly-D-Lysine | 107 | 173 |
| Collagen | 27 | 101 |
| Plastic | 57 | 106 |
| Fibronectin | 47 | 67 |
| Laminin | 0 | 20 |

EXAMPLE 5

The Use of Bioadhesive Polyphenolic Protein on Artificial Vascular Implants

Polytetrafluoroethylene (PTFE) is a substrate commonly used for vascular implants. The major problem with the use of this material is that the seeding of vascular cells on PTFE is very difficult due to its high hydrophobicity. For many implants, a confluent cell monolayer on its surface would prevent clot formation. To test the effectiveness of bioadhesive polyphenolic protein to act as a mediator for attachment of endothelial cells to PTFE, the vascular implant material was coated with 200 µg per $CM^2$ of bioadhesive polyphenolic protein (Formulation 2). Five hundred thousand endothelial cells were then allowed to attach to the bioadhesive polyphenolic protein. The cells were also seeded onto Teflon ® without coating with bioadhesive polyphenolic protein; and Teflon ® coated with bioadhesive polyphenolic protein without seeding of cells acted as a control. Following 15 minutes of attachment, excess cells were rinsed from the vascular implant material and the vascular implants were fixed with formalin, stained with crystal violet, and dried as described in Example 4. The results of this example appear in FIG. 5 and demonstrate that, although some staining can be seen on both Teflon ® treated with bioadhesive polyphenolic protein without cells (Sample 1) and on Teflon ® that is untreated with adhesive, but is seeded with cells (Sample 2), by far the greatest staining, or cell attachment, occurred on the treated Teflon ® containing the endothelial cells (Sample 3). Thus, bioadhesive polyphenolic proteins enhance the seeding of vascular implants with endothelial cells, thereby providing a mechanism by which clot formation may be minimized or eliminated following vascular implant surgery.

EXAMPLE 6

Method for extraction of 45% Pure Bioadhesive Polyphenolic Protein 300 grams of marine mussel, M. edulis, feet are combined with 900 mls of neutral salt buffer which contains 1M sodium chloride, 0.05M tris(hydroxymethyl)aminomethane (pH 7.5), 1 mM phenylmethylsulfonylfluoride, 10 mM N-ethylmaleimide, 0.025M ethylenediamine tetraacetic acid and 1 mM potassium cyanide plus 9 mls of antifoam concentrate in a commercial blender on high speed and thoroughly blended, precipitating the bioadhesive polyphenolic protein. The mixture is centrifuged at 10K rpm for 15 minutes. The pellet is re-suspended in 900 mls of 5% acetic acid using the blender on high speed. Bioadhesive polyphenolic protein remains in the supernatant during centrifugation at 10K rpm for 45 minutes. The approximately 1000 mls of supernatant is put into an ice bath with continual stirring. 5 mls of 2M sodium borate plus 95 mls of 5M sodium chloride are added to the stirring supernatant. This mixture is centrifuged at 10K rpm for 15 minutes. The new supernatant is treated identically as above with the addition of four times as much 2M sodium borate and 5M sodium chloride. Once again, the mixture is centrifuged at 10K for 15 minutes. The pellet is re-suspended in the following mixture: 7.5 mls of 2M sodium borate, 50 mls of 5M sodium chloride, 50 mls of distilled water, 37.5 mls of 8M urea in 5% acetic acid, and 5.6 mls of concentrated acetic acid. The mixture is slowly stirred for approximately 16 hours. The suspension is centrifuged at 10K rpm for 15 minutes. The supernatant is saved and dialyzed (8-12K molecular weight cut-off membranes) against 5% acetic acid for approximately 16 hours. Amino acid analysis establishes that the extract contains 45% pure bioadhesive polyphenolic protein. The purity of the extract is governed by the number of extractions effected. The yield of pure bioadhesive polyphenolic protein decreases as the number of extractions increases. All procedures described herein were conducted at 4° C.

FURTHER CHROMATOGRAPHIC PURIFICATION

Using liquid chromatography, SE Sephadex resins retain polyphenolic proteins in 5.5% Guanidine hydrochloride (GuHCl) in 5% acetic acid. The protein is then eluted from the resin with a gradient of 5.5-20% GuHCl in acetic acid, the peak areas pooled and dialyzed against 5% acetic acid to remove the GuHCl. Storage of the proteins is most stable at 4° C. in 5% acetic acid. Prior to its use as an adhesive, in vivo or in contact with live cells, bioadhesive polyphenolic proteins must be dialyzed against water to raise the pH of the solution to near neutrality and the preparation must be concentrated to between 3 and 10 mg/ml. This is accomplished using an ultrafiltration membrane with pore size exclusion limits of 30,000 or less. This is not necessary when bioadhesive polyphenolic proteins are dried onto an inert substrate prior to use.

EXAMPLE 7

Bioadhesive polyphenolic protein, 45% pure (Formulation 2), was used to immobilize heparin, a mucopolysaccharide having specific anticoagulant properties, and peroxidase, a protein enzyme which oxidizes peroxide. This was done to show that other substances could be efficiently bound to plasticware via a bioadhesive polyphenolic protein intermediate.

For both, 7 µg of bioadhesive polyphenolic protein was dried onto tissue culture plasticware dishes of 2 $cm^2$ area for a final concentration of 3.5 µg/$cm^2$. The protein was washed with 100% ethanol and then twice with water as described in Example 1.

Heparin was added to the dishes at 5 different concentrations: 90, 60, 30, 15 and 5 units/dish. Heparin was also dried onto untreated plastic dishes. All tests were performed in duplicate. The plates were washed with 0.1M phosphate buffer before use to remove loosely bound heparin.

The assay for heparin activity was performed by adding fresh human blood to each dish at 0.5 ml per dish with incubation at 23° C. Clotting times were visually observed and recorded. The results are shown in Table 7.

TABLE 7

| | Clotting Time (minutes)* | |
|---|---|---|
| Units Heparin | With Bioadhesive Polyphenolic Protein | Without Bioadhesive Polyphenolic Protein |
| 90 | **NC | NC |
| 60 | NC | NC |
| 30 | NC | 61,104 |
| 15 | NC | 30,29 |
| 5 | NC | 30,27 |
| 0 | 28, 29 | 13,11 |

*Numbers shown are duplicate assays
**NC = No clotting after 24 hours

Heparin was very effectively immobilized to plastic employing bioadhesive polyphenolic protein. No clotting was observed in 24 hours even at the lowest dose of heparin. All doses below 60 units clotted in 2 hours or less in dishes where heparin was attached directly to plastic. At the higher doses, sufficient heparin binds to the plastic to prevent clot formation.

Peroxidase was immobilized in a similar manner: 5 different concentrations of peroxidase, 1, 0.5, 0.1, 0.05, 0.025 μg/dish, were added to both uncoated plastic dishes and plastic dishes coated with bioadhesive polyphenolic protein (in duplicate). As with heparin, a 0.1M phosphate buffer wash was used to remove loosely bound enzyme.

The assay for peroxidase involves adding a substrate mixture, peroxide plus 0-phenylene diamine (OPD) in phosphate buffered saline. The substrate mix, per ml, contains 100 μl of peroxide (40 μl of 30% peroxide in 50 ml water) plus 100 μl OPD (10.7 mg in 8.56 ml water) and 800 μl phosphate buffered saline. 1 ml is added to each dish. After 5 minutes incubation at 23° C., 100 μl of 4N sulfuric acid is added to stop the reaction. It is a colorimetric assay with a wavelength optimum at 490 nm. The data in duplicate is presented as absorbance units at 490 nm in Table 8.

TABLE 8

| μg Peroxidase | With Bioadhesive Polyphenolic Protein | Without Bioadhesive Polyphenolic Protein |
|---|---|---|
| 1.0 | 1.5, 1.3 | 1.4, 1.2 |
| 0.5 | 0.6, 0.7 | 0.5, 0.5 |
| 0.1 | 0.2, 0.2 | 0.05, 0.06 |
| 0.05 | 0.1, 0.1 | 0.04, 0.04 |
| 0.025 | 0.05, 0.05 | 0.04, 0.04 |

As with heparin, at the higher concentrations no enhancement is seen by employing bioadhesive polyphenolic protein, sufficient enzyme binds to plastic. At the lower concentrations, significant enhancement or recovery is seen by employing bioadhesive polyphenolic protein.

EXAMPLE 8

Bioadhesive polyphenolic protein has been found to successfully serve as a substrate for tissues and cells in histology and cytology. In this example, 45% bioadhesive polyphenolic protein (Formulation 2) was used to affix bovine Descemet's membrane with endothelial cell preparations to glass slides. Whole cornea were removed from freshly killed cows and placed either in physiological saline or in 10% neutral buffered formalin. Descemet's membrane was then removed from the posterior side of the cornea by gentle peeling. The tissue was transferred to slides (pre-cleaned with 5% acetic acid) and coated with 50 μg of bioadhesive polyphenolic protein. Tissue preparations were then dried onto the bioadhesive polyphenolic protein at room temperature or on 55° C. warming plates for twenty minutes. When formalin fixed tissue was used, the tissue was rinsed with saline for removal of excess formalin prior to attachment to the bioadhesive polyphenolic protein. Following drying, tissue-slide preparations were treated with formalin to fix tissues to the bioadhesive polyphenolic protein for five minutes. Tissues treated in this manner were retained on the bioadhesive polyphenolic protein for weeks in aqueous solutions. Furthermore, following extensive agitation by shaking in water, saline, dilute and 100% ethanol, and xylene the tissues still remained intact. In the absence of bioadhesive polyphenolic protein, adherence of tissues to slides did not even survive the first formalin treatment.

What is claimed is:

1. A method of affixing viable cells to a substrate for in vitro culture comprising
    (1) coating a substrate with a sterile formulation comprising polyphenolic protein containing from about 35 to 100% by weight pure bioadhesive polyphenolic protein having the repeating decapeptide unit:

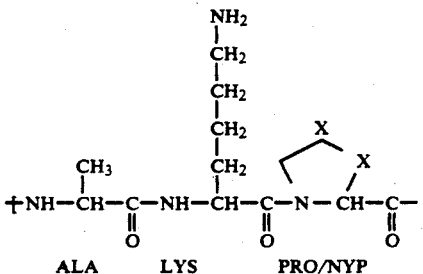

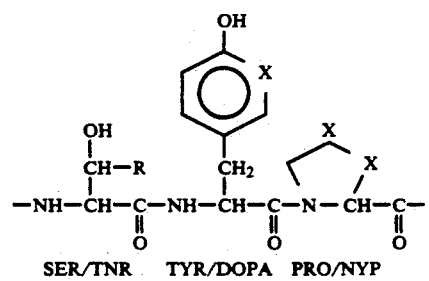

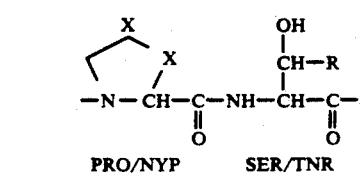

-continued

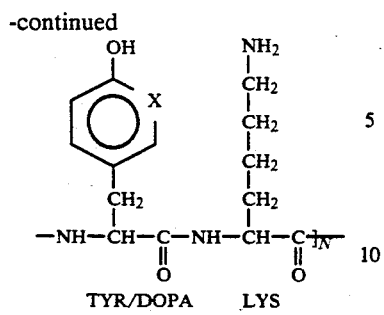

TYR/DOPA  LYS wherein N is a whole number ranging from about 10 to about 100, wherein each X is independently selected from the group consisting of hydroxyl and hydrogen, and wherein each R is independently selected from the group consisting of hydrogen and methyl;

(2) drying said coating on said substrate;
(3) fixing said coating on said substrate;
(4) rinsing said coated substrate to remove extraneous materials not firmly attached to said substrate; and
(5) applying viable mammalian cells to said coated substrate, whereby said cells become affixed to said coated substrate and, in the presence of a nutritive environment, perform normal metabolic cell functions.

2. A method as defined in claim 1 wherein said substrate is coated with from 0.1 to 2 μl of said formulation containing from about 10 to 60 μg/μl of said bioadhesive polyphenolic protein per cm² of substrate.

3. A method as defined in claim 1 wherein said coating is fixed on said substrate by rinsing said substrate with an anhydrous biologically compatible sterilizing medium.

4. A method as defined in claim 3 wherein said sterilizing medium is 30 to 100% ethanol.

5. A method as defined in claim 3 wherein said sterilizing medium is 30–100% isopropanol.

6. A method as defined in claim 1 wherein the coated substrate is rinsed to remove extraneous materials with sterile aqueous serum-free tissue culture medium.

7. A method as defined in claim 1 wherein the coated substrate is rinsed to remove extraneous materials with water or buffer solution.

8. A method as defined in claim 1 wherein the viable cells are applied to the coated substrate in a serum-containing medium.

9. A method as defined in claim 1 wherein the viable cells are applied to said coated substrate in a serum-free medium.

10. A method as defined in claim 1 wherein said substrate is an in vitro substrate.

11. A method as defined in claim 10 wherein said substrate is selected from the group consisting of synthetic polymeric materials, glass, metals, and microporous filters.

12. A method as defined in claim 11 wherein said substrate is polytetrafluoroethylene.

13. A method as defined in claim 11 wherein said substrate is an in vivo substrate.

14. A method as defined in claim 13 wherein the substrate is selected from the group consisting of collagen, laminin, fibronectin, prosthetic grafting materials and polylysine.

15. A method as defined in claim 14 wherein said substrate is polytetrafluoroethylene.

16. An in vitro cell culturing system comprising: a substrate; a coating thereon of a sterile formulation comprising polyphenolic protein containing from about 35 to 100% by weight pure bioadhesive polyphenolic protein having the repeating decapeptide unit:

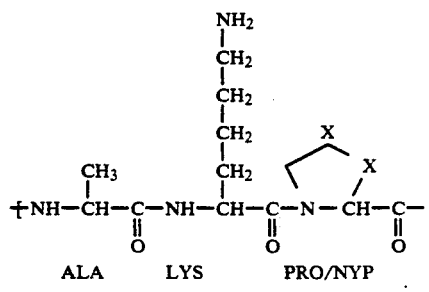

ALA  LYS  PRO/NYP

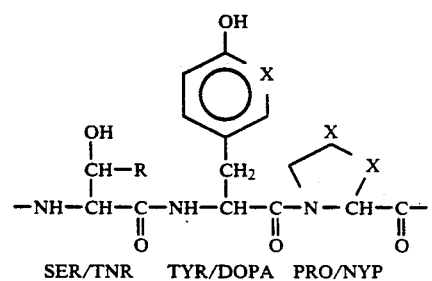

SER/TNR  TYR/DOPA  PRO/NYP

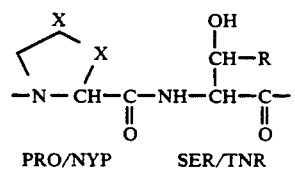

PRO/NYP  SER/TNR

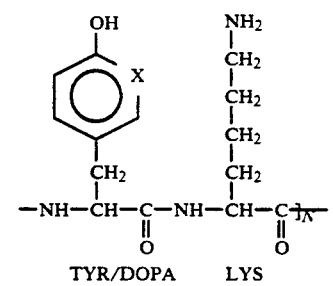

TYR/DOPA  LYS wherein N is a whole number ranging from about 10 to about 100, wherein each X is independently selected from the group consisting of hydroxyl and hydrogen, and wherein each R is independently selected from the group consisting of hydrogen and methyl; viable mammalian cells affixed to said coated substrate; and a nutritive medium contacting said cells, whereby said cells perform normal metabolic cell functions.

17. A cell culturing system as defined in claim 16 wherein the substrate is an in vitro substrate.

18. A cell culturing system as defined in claim 17 wherein the substrate is selected from the group consisting of synthetic polymeric material, glass, metals, and microporous filters.

19. A cell culturing system as defined in claim 18 wherein said substrate is polytetrafluoroethylene.

20. A cell culturing system as defined in claim 16 wherein said substrate is an in vivo substrate.

21. A cell culturing system as defined in claim 20 wherein the substrate is selected from the group consisting of collagen, laminin, fibronectin, prosthetic grafting materials and polylysine.

22. A cell culturing system as defined in claim 21 wherein the substrate is polytetrafluoroethylene.

23. A method as defined in claim 1, wherein the bioadhesive polyphenolic protein contains about 45% pure bioadhesive polyphenolic protein and is obtained from the marine mussel *Mytilus edulis*.

24. A cell culturing system according to claim 16, wherein the bioadhesive polyphenolic protein contains about 45% pure bioadhesive polyphenolic protein and is obtained from the marine mussel *Mytilus edulis*.

* * * * *